United States Patent [19]

Becherer et al.

[11] Patent Number: 4,714,766
[45] Date of Patent: Dec. 22, 1987

[54] PROCESS FOR THE PREPARATION OF 2-CHLOROBENZOXAZOLES

[75] Inventors: Johannes Becherer, Maintal; Reinhardt Handte, Gablingen; Hans J. Nestler, Königstein/Ts; Ulrich Kussmaul, Karben, all of Fed. Rep. of Germany

[73] Assignee: Cassella Aktiengesellschaft, Frankfurt am Main, Fed. Rep. of Germany

[21] Appl. No.: 885,148

[22] Filed: Jul. 14, 1986

Related U.S. Application Data

[63] Continuation of Ser. No. 647,439, Sep. 5, 1984, abandoned.

[30] Foreign Application Priority Data

Sep. 23, 1983 [DE] Fed. Rep. of Germany ....... 3334417

[51] Int. Cl.[4] ............................................ C07D 263/54
[52] U.S. Cl. .................................... 548/217; 548/221
[58] Field of Search ................. 548/217, 221; 260/694

[56] References Cited

U.S. PATENT DOCUMENTS

3,284,294 11/1966 Sasse et al. ......................... 548/217

FOREIGN PATENT DOCUMENTS

6036474 4/1981 Japan ................................... 548/221
7134470 8/1982 Japan ................................... 548/221
1209054 10/1969 U.S.S.R. ............................. 548/221

OTHER PUBLICATIONS

Barton et al., Comprehensive Organic Chemistry, vol. 4, Pergamon Press, New York (1979) pp. 119, 120, 551.
Tanaka et al., "Studies on Furan Derivatives III., . . . ," Chem. Pharm. Bull. 26 (1978) pp. 3576-3579.
Nippon; 3-,4,5,6,7-Pentachloro-1,2,-Benzisothiazolel, 1-Dioxide," Chem. Abst. 96:142840e (1982).
Yarchen Ko et al., "Reaction of Phosphorus Pentachloriden; " Chem, Abst, 98: 142999(e) (1983).

Primary Examiner—Donald G. Daus
Assistant Examiner—Cecilia Shen
Attorney, Agent, or Firm—Connolly & Hutz

[57] ABSTRACT

The process for the preparation of 2-chlorobenzoxazoles of the formula

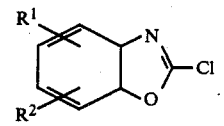

wherein $R^1$ and $R^2$, independently of one another, are hydrogen or halogen comprising reacting a benzoxazolinone of the formula

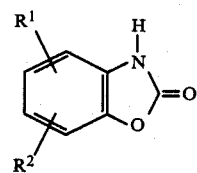

with a molar excess of phosphorus pentachloride.

9 Claims, No Drawings

PROCESS FOR THE PREPARATION OF 2-CHLOROBENZOXAZOLES

This is a continuation of application Ser. No. 647,439 filed Sept. 5, 1984 now abandoned.

The present invention relates to a process for the preparation of 2-chlorobenzoxazoles of the formula I

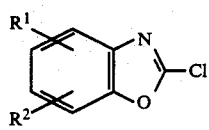

in which the symbols $R^1$ and $R^2$, independently of one another, denote hydrogen or halogen, in which benzoxazolinones of the formula

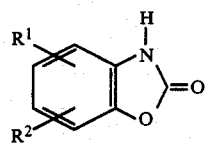

are reacted with phosphorus pentachloride.

It is possible for the halogen atoms represented, where appropriate, by $R^1$ and $R^2$ to be, independently of one another, preferably fluorine, chlorine or bromine atoms, in particular chlorine atoms. If only $R^1$ represents halogen but $R^2$ represents hydrogen, the halogen atom can occupy positions 4, 5, 6 or 7 of the benzoxazole; if $R^1$ and $R^2$ are both halogen atoms, they can be located in the 4,5-, 4,6-, 4,7-, 5,6-, 5,7- or 6,7-positions. When the benzo nucleus of the benzoxazole is substituted once, positions 5 and, in particular, 6 are preferred, and when it is substituted twice, the 5,7-position is particularly preferred.

2-Chlorobenzoxazoles of the formula I are valuable intermediates for the synthesis of plant-protection agents.

The preparation of the 2-chlorobenzoxazoles of the formula I has hitherto invariably been carried out starting with the corresponding 2-mercaptobenzoxazoles, by replacement of the mercapto group by chlorine using chlorinating agents. Thus, according to the data in J. pr. Chemie 42, 454 (1), 2-chlorobenzoxazole is obtained by heating the corresponding 2-mercato compound with phosphorus pentachloride, which should, where possible, be employed in less than the stoichiometric amount, without a solvent or diluent. In this process, carbonisation occurs toward the end of the reaction; the yields are very low and a variety of byproducts are obtained, some of which are difficult to separate out. Examples of other chlorinating agents which can be used to replace the 2-mercapto group in 2-mercaptobenzoxazole by chlorine are disulphur dichloride (Boll. Sci. Fac. Chim. Ind. Bologna 23 (2-3) 89–98 (1965)), phosgene (German Patent Specification No. 1,164,413) or even elementary chlorine (Am. Chemical Journal 21, 123 (1899)). The disadvantage common to the known processes mentioned is that the starting materials used are the corresponding 2-mercaptobenzoxazoles. In preparing them from the corresponding 2-aminophenols, elaborate safety regulations have to be observed because of the necessity of using, and because of the partial elimination of, carbon disulphide, so that it is thoroughly desirable to replace 2-mercaptobenzoxazole by less costly starting materials. A further disadvantage of the known processes mentioned is that byproducts unavoidably result, and some of them are not straight-forward to dispose of and some of them are difficult to separate out.

Recently, there has even been described a process for the preparation of 2-chlorobenzoxazole from benzoxazolinone (compare Zeitschrift fur Chemie 5 (1965), page 178). According to the data in this publication, the replacement of the carbonyl group by chlorine takes place by reacting the starting material with a special chlorinating agent, catechylphosphoric trichloride. However, because of side reactions which take place simultaneously, the yield in this process is very unsatisfactory; it is only 42% of theory according to the data in the publication.

Isolation of the desired 2-chlorobenzoxazole is accordingly difficult.

It has now been found, surprisingly, that 2-chlorobenzoxazoles of the formula I can be obtained in a simple manner and in good yield by reacting benzoxazolinones of the formula II with phosphorus pentachloride, when care is taken that there is always a certain excess of phosphorus pentachloride compared with benzoxazolinone of the formula II in the reaction mixture.

For technical reasons, it is advantageous to work in a solvent or diluent so as to produce a homogeneous reaction mixture and for the reaction to take place smoothly. The reaction is advantageously carried out at temperatures between 120° and 200° C., preferably 140° and 180° C. Suitable solvents are inert, aromatic hydrocarbons, such as, for example, benzene, toluene, xylene and technical mixtures of xylenes, preferably halogenated hydrocarbons, such as, for example, monochlorobenzene, o-dichlorobenzene, trichlorobenzene and chlorotoluene, and, last but not least, phosphorus oxychloride.

If solvents having boiling points below the desired reaction temperature are used, then the process should be carried out in a closed vessel under pressure in a manner known per se.

The essential criterion for the process according to the invention is the reaction of the benzoxazolinones with the phosphorus pentachloride which is present in excess. This can be achieved by heating the benzoxazolinone together with a relatively large molar excess of, for example, 2 to 10 moles of phosphorus pentachloride per mole of benzoxazolinone to the reaction temperature. It is more advantageous initially to introduce phosphorus pentachloride in a solvent or diluent and, at the desired reaction temperature, gradually to meter in the benzoxazolinone as the solid, or a suspension or solution.

It has proved to be particularly advantageous in the process according to the invention to use 2 to 10 moles, in particular 3 to 5 moles, of phosphorus pentachloride per mole of benzoxazolinone of the formula II to be reacted.

Accordingly, a particularly preferred embodiment of the process according to the invention comprises heating, to a reaction temperature between 120° and 200° C., preferably 140° to 170° C., 2 to 10 moles, preferably 3 to 5 moles, of phosphorus pentachloride per mole of benzoxazolinone to be reacted, in an inert solvent, preferably a relatively high boiling halogenated aromatic solvent, such as, for example, o-dichlorobenzene, and introducing, in portions or, preferably, continuously, the benzoxazolinone.

As a rule, the reaction is complete after a short time. When carrying out the process by the particularly preferred embodiment described above, the introduction of the benzoxazolinone can be carried out as quickly as is permitted by the evolution of hydrogen chloride which occurs. After the introduction of the benzoxazolinone is complele. subsequent heating for about 3 to 15 minutes is sufficient to complete the reaction.

The working up of the reaction mixture after the reaction is carried out in a manner known per se, advantageously by fractional distillation. However, when a relatively large excess of phosphorus pentachloride is used, it is advantageous briefly to cool the reaction mixture to temperatures between 0° and 30° C. before distillation, since, when the solvent is appropriately selected, for example when o-dichlorobenzene is used, this results in the major part of the excess phosphorus pentachloride crystallising out of the mixture, and this can be isolated in a particularly straightforward manner by filtration with suction and can be used again.

Using the process according to the invention, it is possible to prepare, in good yields and in very high purity, 2-chlorobenzoxazoles of the formula I from starting materials which are industrially relatively readily accessible. The isolation of the final products is carried out by fractional distillation, which is straightforward to carry out industrially, preferably under reduced pressure. Excess chlorinating agent and solvent used can readily be regenerated in this manner. Thus the process overall operates very considerably more economically than processes hitherto known for the preparation of 2-chlorobenzoxazoles.

The process according to the invention is particularly valuable for the preparation of 2-chlorobenzoxazoles of the formula I, in which $R^1$ denotes halogen, in particular chlorine, and $R^2$ represents hydrogen, which are necessary as intermediates for the preparation of plant-protection agents. The halogen representing $R^1$, in particular chlorine, is preferably in the 6-position.

Benzoxazolinones of the formula II which are required as starting materials for the process according to the invention are readily accessible from the corresponding substituted o-aminophenols by reaction with carbonic acid derivatives in a known manner, and some of them are prepared on a large scale industrially.

In carrying out the inventive process, the 6-chlorobenzoxazolin-2-one required as starting product for preparing the 2,6-dichlorobenzoxazole need not be employed in its isolated form but can be used in the form of a raw reactive mixture formed in the ring chlorination of benzoxazolin-2-one in an organic solvent. This reaction mixture is, as a rule, a suspension.

The ring chlorination of benzoxazolin-2-one, i.e. its conversion into 6-chlorobenzoxazolin-2-one, is carried out with a suitable chlorinating agent, usually elemantary chlorine or sulfuryl chloride, in an inert organic solvent at temperatures from 0° to 15° C., preferably 20° to 120° C. Suitable inert organic solvents are, above all, the halogenated aromatic hydrocarbons already mentioned, preferably o-dichlorobenzene. In the ring chlorination of benzoxazolin-2-one to give 6-chlorobenzoxazolin-2-one the ring chlorinating agent is used in a 1.0 to 1.3 molar, preferably 1.0 to 1.1 molar, amount.

The reaction mixture formed in the ring chlorination of benzoxazolin-2-one does not have to be worked up or purified for the subsequent conversion with an excess of phosphorus pentachloride, but can be directly reacted with an excess of phosphorus pentachloride using the inventive process. This may be done, for example, by adding the phosphorus pentachloride to the ring chlorination mixture or, advantageously, by initially placing the excess of phosphorus pentachloride in an inert organic solvent and gradually metering in the ring chlorination mixture at the desired reaction temperature.

The benzoxazolin-2-one reguired for the ring chlorination, likewise, does not have to be employed in its pure form but may be used for the ring chlorination in the form of a raw cyclizing solution which is obtained in the cyclization of 2-aminophenol with a carbon dioxide derivative in a halogenated aromatic hydrocarbon, preferably o-dichlorobenzene.

Examples of suitable carbon dioxide derivatives for this cyclization reaction are carbamic acid chloride, urethanes of the formula $O=C(NH_2)OR$, chloroformic esters of the formula $O=C(Cl)OR$, carbonic esters of the formula $O=C(OR)_2$ or $O=C(OR)OR'$, where R and R' denote in particular alkyl, preferably alkyl having 1 to 4 carbon atoms. However, posgene and urea are particularly suitable carbon dioxide derivatives for the cyclization reaction.

This cyclization reaction of 2-aminophenol with carbon dioxide derivatives, such as phosgene or urea, to give benzoxazolin-2-one is carried out under a protective gas atmosphere at temperatures above 100° C., e.g. 100° to 190° C., 1 to 1.3 mole of the carbon dioxide derivative being employed per mole of 2-aminophenol. If urea is used as cyclizing agent it may be appropriate to distil part of the solvent off the cyclization solution prior to the subsequent ring chlorination reaction in order to completely remove the ammonia generated as a byproduct from the reaction mixture.

A particularly preferred embodiment of the inventive process for preparing 2,6-dichlorobenzoxazole thus resides in that benzoxazolin-2-one is reacted, if appropriate in the form of a raw cyclization mixture, in a halogenated aromatic hydrocarbon, preferably o-dichlorobenzene, with 1.0 to 1.3 molar, preferably 1.0 to 1.1 molar amounts of a ring chlorinating agent and the suspension obtained is subsequently metered in in portions or preferably continuously to a solution, which has been heated to 120° to 200° C., preferably 140° to 180° C., of the 2 to 10 fold, preferably 3 to 5 fold, molar amount of phosphorus pentachloride in the same solvent. In this case, too, the metering operation is carried out sufficiently fast that the temperature is not lower than required and that the hydrogen chloride generated can be removed. The metering operation having ended, in this case, too, a further heating of 3 to 15 minutes is sufficient to complete the reaction. In the preparation of 2,6-dichlorobenzoxazole, starting from benzoxazolin-2-one using the two step process described, the only byproducts generated are, likewise, the gaseous compounds hydrogen chloride and (only if sulfuryl chloride is used as ring chlorinating agent) sulfur dioxide which can easily be absorbed, as well as the phosphorus oxychloride which can easily be eliminated during distillation. The two-step process is thus also considerably more unobjectionable from an economical and ecological point of view than the hitherto known process for preparing 1,6-dichlorobenzoxazole.

In the two-step process for preparing 2,6-dichlorobenzoxazole the high degree of product purity and yield over the yield obtained with the conversion of a pure isolated 6-chlorobenzoxazolin-2-one with phosphorus pentachloride is particularly surprising. In the literature yields of about 90% are given for the preparation of 6-chlorobenzoxazolin-2-one by ring chlorination of benzoxazolin-2-one if chlorine is used, and 81% if sulfuryl chloride is used. Consequently, one should observe, in the further reaction of a raw chlorination mixture, a correspondingly reduced yield over the reaction of the isolated pure substance and a product purity reduced by isomeric byproducts. It was not foreseeable that the 2,6-dichlorobenzoxazole obtained in the inventive process using 6-chlorobenzoxazolin-2-one in the form of a raw chlorination mixture is of almost equal purity (content of 2,6-dichlorobenzoxazole over 99%, determined by gas chromatography) and in a yield which is lower by 2% only over the process starting from the pure 6-chlorobenzoxazolin-2-one. If in the preparation of 2,6-dichlorobenzoxazole, instead of benzoxazolin-2-one a raw cyclization mixture in an inert organic solvent of 2-aminophenol and a carbon dioxide derivative is used, the yield of 2,6-dichlorobenzoxazole is slightly lower but its purity is still greater than 95%. The exemplary embodiments which follow illustrate the procedure for the process according to the invention (GC denoting gas chromatogram):

EXAMPLE 1

1 litre of o-dichlorobenzene and 625 g (3 moles) of phosphorus pentachloride are heated to 160° C., then 169.5 g (1 mole) of solid 6-chlorobenzoxazolin-2-one are introduced in small portions over the course of 60 minutes, vigorous evolution of hydrogen chloride occuring for a short time after each portion. The mixture is then stirred for a further 15 minutes at 150°–160° C., and then cooled to 0° C., whereupon the major part of the excess pCl$_5$ crystallises out. The phosphorus pentachloride precipitate is filtered off with suction, Washed with a little cold o-dichlorobenzene, and the filtrate is fractionated under reduced pressure. phosphorus oxychloride distils over first, then o-dichlorobenzene together with the remainder of the excess phosphorus pentachloride, and last, at about 110° C. and 17.3 mbar, 2,6-dichlorobenzoxazole. About 136 g of 2,6-dichlorobenzoxazole of melting point 48–49° C. are obtained. GC purity 99.7%. yield: 72% of theory.

The recovered phosphorus pentachloride and o-dichlorobenzene can be used again for the next batch.

EXAMPLE 2

If the process is carried out as in Example 1, but 1,040 g (5 moles) of phosphorus pentachloride are used in place of 625 g (3 moles), then 145 g of 2,6-dichlorobenzoxazole are obtained, corresponding to a yield of 77% of theory.

EXAMPLE 3

If the process is carried out as in Example 1, but recovered phosphorus pentachloride, which is about 90% pure and moist with o-dichlorobenzene, and re-covered o-dichlorobenzene are used, then 2,6-dichlorobenzoxazole is obtained in the same yield and purity as in Example 1.

EXAMPLE 4

If the process is carried out as in Example 1, but only 500 ml of o-dichlorobenzene is initially introduced, and the 6-chlorobenzoxazolin-2-one is metered in as a suspension in 500 ml of o-dichlorobenzene, then 2,6-dichlorobenzoxazole is obtained in the same yield and purity as in Example 1.

EXAMPLE 5

If the process is carried out as in Example 1, but, instead of 6-chlorobenzoxazolin-2-one, the same amount of 5-chlorobenzoxazolin-2-one is used, then about 130 g, corresponding to 69% of theory, of 2,5-dichlorobenzoxazole, melting point 46°–48° C., are obtained.

EXAMPLE 6

In analogy to Example 1, 204 g of 5,7-dichlorobenzoxazolin-2-one, in place of 6-Chlorobenzoxazolin-2-one, are reacted. 2,5,7-Trichlorobenzoxazole of melting point 140°–142° C. is obtained in a yield of 68% of theory by recrystallisation, from toluene or ligroin, of the residue remaining after distilling out the o-dichlorobenzene.

EXAMPLE 7

500 ml of o-dichlorobenzene and 625 g (3 moles) of phosphorus pentachloride are heated to 150° C., then, at an internal temperature of 140°–150° C., 151 g (1 mole) of benzoxazolin-2-one, suspended in 500 ml of o-dichlorobenzene, are metered in over the course of 30 minutes. The mixture is then stirred at 140° C. for 5 minutes and then rapidly cooled to 5° C., whereupon the major part of the excess phosphorus pentachloride crystallises out. The phosphorus pentachloride precipitate is filtered off with suction, washed with a little cold o-dichlorobenzene, and the filtrate is fractionated under reduced pressure. Phosphorus oxychloride distils over first, then o-dichlorobenzene together with the remainder of the excess phosphorus pentachloride, and last about 115 g (75% of theory) of 2-chlorobenzoxazole of boiling point 104°–107° C. at 30.6 mbar.

EXAMPLE 8

135 g (1 mole) of dry benzoxazolin-2-one are suspended in 600 ml of o-dichlorobenzene at room temperature. 142 g (1.05 mole) of sulfuryl chloride are added dropwise in the course of 1 hour, the interior temperature rising to about 40° C. The mixture is stirred for a further 10 hours at 40° C., then heated to 90° C. in the course of 3 hours and stirring is continued for a further hour. The raw mixture 1 is obtained.

1,040 g (5 moles) of phosphorus pentachloride are heated to 150° to 160° C. with 400 ml of o-dichlorobenzene. For doing so, the raw mixture 1 is metered in with heating within 2 hours such that the interior temperature does not drop below 150° C. The addition being complete, the mixture is stirred for a further 10 minutes, then cooled to 10° C., the phosphorus pentachloride which has precipitated is filtered off with suction and is washed with a little cold o-dichlorobenzene. When fractionating the filtrate under reduced pressure via a 15 cm column with Raschig rings, phosphorus oxychloride distils over first, then o-dichlorobenzene together with the excess of phosphorus pentachloride, and last 2,6-dichlorobenzoxazole at about 110° C. and at 17.3 mbar. The yield is 141 g corresponding to 75% of theory, relative to benzoxazolin-2-one used. GC purity of the product: 99.3%. Content of 2-chlorobenzoxazole: 0.3%; content of 2,5-dichlorobenzoxazole: 0.1%.

EXAMPLE 9

400 ml of o-diohlorobenzene and 1,040 g (5 moles) of phosphorus pentachloride are heated to 150° to 160° C. Then 169.5 g (1 mole) of 6-chlorobenzoxazolin-2-one, suspended in 600 ml of o-dichlorobenzene, are metered in within 2 hours with heating such that the interior temperature does not drop below 150° C. The addition being complete, stirring is continued for a further 10 minutes. working up analogously to Example 8 results in a yield of 145 g of 2,6-dichlorobenzoxazole, corresponding to 77% of theory. GC purity: 99.7%.

EXAMPLE 10

If the process is carried out as in Example 8, but the corresponding amounts of recovered phosphorus pentachloride and o-dichlorobenzene are used in the second stage, then 2,6-dichlorobenzoxazole is obtained in the same yield and purity.

EXAMPLE 11

135 g (1 mole) of dry benzoxazolin-2-one are suspended in 600 ml of o-dichlorobenzene. 75 g (1.05 mole) of chlorine are introduced at 100° C. within 2 hours, The hydrogen chloride which escapes is absorbed in water.

The raw mixture is reacted with phosphorus pentachloride and worked up analogously to Example 8. 138 g (73% of theory) of 2,6-dichlorobenzoxazole in comparable purity are obtained.

EXAMPLE 12

109 g (1 mole) of 2-aminophenol and 63 g (1.05 mole) of urea are suspended in 350 ml of o-dichlorophenol and the suspension is heated to 150° to 160° C. under nitrogen for 3 hours, ammonia escaping. About 100 ml of the solvent are distilled off by a slight lowering of the pressure and subsequently 300 ml of fresh o-dichlobenzene are added. At an interior temperature of 110° C. 78 g (1.1 mole) of chlorine are then passed in within 1 to 2 hours, hydrogen chloride escaping. The raw mixture is reacted with phosphorus pentachloride and worked up analogously to Example 8. 115 g (61% of theory) of 2,6-dichlorobenzoxazole are obtained. GC purity: 96.8%.

EXAMPLE 13

109 g (1 mole) of 2-aminophenol are suspended in 350 ml of o-dichlorobenzene and the suspension is heated under nitrogen to 120° C. At this temperature 119 g (1.2 mole) of phosgene are introduced within about 2 hours. The batch is cooled to 40° C.

Then 162 g (1.2 mole) of sulfuryl chloride are added dropwise within half an hour and stirring is effected for 10 hours at 40° C. and for 1 hour at 90° C. The raw mixture is reacted with phosphorus pentachloride and worked up analogously to Example 8. 92 g (49% of theory) of 2,6-dichlorobenzoxazole are obtained. GC purity: 95.9%.

What is claimed is:

1. The process for the preparation of 2-chlorobenzoxazoles of the formula

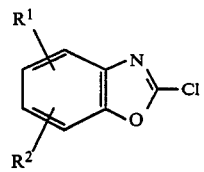

wherein $R^1$ and $R^2$, independently of one another, are hydrogen or halogen, which comprises introducing a benzoxazolinone of the formula

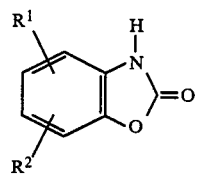

in portions or continuously to a 120° to 200° C. hot solution of 2 to 10 moles per mole of the benzoxazolinone of phosphorus pentachloride in an enert solvent.

2. The process according to claim 1 wherein the amount of phosphorus pentachloride is 3 to 5 moles per mole of the benzoxazolinone.

3. The process according to claim 1 wherein the temperature of the reaction is from 140° to 170° C.

4. The process according to claim 1 wherein the benzoxazolinone is a raw reaction mixture formed in the ring chlorination of benzoxazolin-2-one in an orgainic solvent and containing 6-chlorobenzoxazolin-2-one.

5. The process according to claim 1 wherein the amount of phosphorus pentachloride in 3 to 5 moles per mole of the benzoxazolinone and the temperature of the reaction is from 140° to 170° C.

6. The process according to claim 1 wherein $R^1$ is halogen and $R^2$ is hydrogen.

7. The process according to claim 1 wherein $R^1$ is chloro and $R^2$ is hydrogen.

8. The process for the preparation of 2,6-dichlorobenzoxazole, which comprises reacting benzoxazolin-2-one in a halogenated aromatic hydrocarbon with 1.0 to 1.3 molar amounts of a ring chlorinating agent and the suspension obtained is subsequently metered in portions or continuously to a solution of 2 to 10 foldmolar amount of phosphorus pentachloride in the same solvent at 120° to 200° C.

9. The process according to claim 8 wherein the benzoxazolin-2-one is reacted in o-dichlorobenzene and the suspension obtained after the ring chlorination is continuously metered into a solution, has been heated to 140° to 180° C. of the 3 to 5 fold molar amount of phosphorus pentachloride in o-dichlorobenzene.

* * * * *

UNITED STATES PATENT AND TRADEMARK OFFICE
CERTIFICATE OF CORRECTION

PATENT NO.  :  4,714,766

DATED  :  DECEMBER 22, 1987

INVENTOR(S) :  BECHERER ET AL

Page 1 of 2

It is certified that error appears in the above-identified patent and that said Letters Patent is hereby corrected as shown below:

On the face of the patent at [56] Other Publications, "Benzisothiazole1, 1-Dioxide" should read --Benzisothiazole 1,1-Dioxide--.

Column 3, line 9, "complele" should read --complete--.

Column 3, lines 57-58, "elemantary" should read --elementary--.

Column 3, lines 59-60, "at temperatures from 0° to 15°C, preferably 20° to 120°C" should read --at temperatures from 0° to 150°C, preferably 20° to 120°C--.

Column 4, line 9, reguired" should read --required--.

Column 4, line 61, "1,6-dichlorobenzoxazole" should read --2,6-dichlorobenzoxazole--.

Column 5, line 35, "pCl$_5$" should read --PCl$_5$--.

Column 7, line 3, "o-diohlorobenzene" should read --o-dichlorobenezene--.

Column 8, line 29, "enert" should read --inert--.

Column 8, line 37 "orgainic" should read --organic--.

UNITED STATES PATENT AND TRADEMARK OFFICE
CERTIFICATE OF CORRECTION

PATENT NO. : 4,714,766

DATED : December 22, 1987

INVENTOR(S) : Becherer et al

It is certified that error appears in the above-identified patent and that said Letters Patent is hereby corrected as shown below:

Column 8, line 58, ",has been heated" should read --, which has been heated--.

Signed and Sealed this

Ninth Day of April, 1991

Attest:

HARRY F. MANBECK, JR.

*Attesting Officer*     Commissioner of Patents and Trademarks